US00PP21070P2

(12) United States Plant Patent
Hooijman

(10) Patent No.: US PP21,070 P2
(45) Date of Patent: Jun. 22, 2010

(54) ROSE PLANT NAMED 'ESM GUINDA'

(50) Latin Name: *Rosa hybrida*
Varietal Denomination: Esm Guinda

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 12/319,411

(22) Filed: Jan. 7, 2009

(51) Int. Cl.
*A01H 5/00* (2006.01)

(52) U.S. Cl. ..... Plt./139

(58) Field of Classification Search ..... Plt./139, Plt./140
See application file for complete search history.

(56) References Cited

OTHER PUBLICATIONS

Upov-rom GTITM Plant Variety Database 2009/04, GTI Jouve Retrieval Software, Citation for *Rosa* 'Esm Guinda', one page.*

* cited by examiner

*Primary Examiner*—June Hwu
(74) *Attorney, Agent, or Firm*—C. A. Whealy

(57) ABSTRACT

A new and distinct cultivar of Rose plant named 'Esm Guinda', characterized by its long, strong and upright flowering stems; durable foliage; red-colored flowers; and excellent postproduction longevity.

1 Drawing Sheet

Botanical designation: *Rosa hybrida*. Cultivar denomination: 'Esm Guinda'.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'Esm Guinda'.

The new Rose plant is a product of a planned breeding program conducted by the Inventor in El Quinche, Pichincha, Ecuador. The objective of the breeding program was to develop new freely-flowering cut flower Rose varieties with novel and attractive flower colors and excellent postproduction longevity.

The new Rose plant originated from a cross-pollination made by the Inventor in September, 2004 of a proprietary Rose selection identified as code number 108, not patented, as the female, or seed, parent with a proprietary Rose selection identified as code number 129, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in April, 2005.

Asexual reproduction of the new Rose plant by cuttings at El Quinche, Pichincha, Ecuador since July, 2005, has shown that the unique features of this new Rose plant are stable and reproduced true to type in successive generations of asexual reproduction.

SUMMARY OF THE INVENTION

The following traits have been repeatedly observed and are determined to be the unique characteristics of 'Esm Guinda'. These characteristics in combination distinguish 'Esm Guinda' as a new and distinct cultivar:

1. Long, strong and upright flowering stems.
2. Durable foliage.
3. Red-colored flowers.
4. Excellent postproduction longevity.

Plants of the new Rose differ from plants of the female parent selection in the following characteristics:

1. Plants of the new Rose have fewer thorns than plants of the female parent selection.
2. Plants of the new Rose have smaller flowers than plants of female parent selection.

Plants of the new Rose differ from plants of the male parent selection in the following characteristics:

1. Plants of the new Rose are taller than plants of the male parent selection.
2. Plants of the new Rose are more freely flowering than plants of the male parent selection.
3. Plants of the new Rose have larger flowers than plants of male parent selection.

Plants of the new Rose can be compared to plants of Rose 'Freedom', not patented. In side-by-side comparisons conducted in El Quinche, Pichincha, Ecuador, plants of the new Rose differed from plants of 'Freedom' in the following characteristics:

1. Plants of the new Rose were more vigorous and had stronger stems than plants of 'Freedom'.
2. Plants of the new Rose had smaller leaves and leaflets than plants of 'Freedom'.
3. Plants of the new Rose flowered earlier and more freely than plants of 'Freedom'.
4. Plants of the new Rose had fewer petals per flower than plants of 'Freedom'.

BRIEF DESCRIPTION OF THE PHOTOGRAPHS

The accompanying colored photographs illustrate the overall appearance of the new Rose plant, showing the colors as true as it is reasonably possible to obtain in colored reproductions of this type. Colors in the photographs may differ slightly from the color values cited in the detailed botanical description which accurately describe the colors of the new Rose.

The photograph at the upper left of the sheet comprises a side perspective view of a typical flowering stem of 'Esm Guinda'.

The photograph at the lower left of the sheet is a close-up view of typical flowers of 'Esm Guinda'.

The photographs at the top right of the sheet is a close-up view of a typical flower and the upper and lower surfaces of typical petals of 'Esm Guinda'.

The photographs at the lower right of the sheet are close-up views of the upper and lower surfaces of typical leaves of 'Esm Guinda'.

DETAILED BOTANICAL DESCRIPTION

Plants of the new Rose have not been observed under all possible environmental conditions. The phenotype may vary somewhat with variations in environment such as temperature and light intensity, without, however, any variance in genotype. The aforementioned photographs, following observations and measurements describe plants grown in El Quinche, Pichincha, Ecuador, in a polyethylene-covered greenhouse and under commercial production practices. Plants were pinched about 13.5 weeks after planting. Plants were about 30 months old when the photographs and description were taken. During the production of the plants, day temperatures ranged from about 16° C. to 30° C., night temperatures ranged from about 12° C. to 16° C. and light levels ranged from about 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'Esm Guinda'.

Parentage:

*Female, or seed, parent.*—Proprietary seedling selection of *Rosa hybrida* identified as code number 108, not patented.

*Male, or pollen, parent.*—Proprietary seedling selection of *Rosa hybrida* identified as code number 129, not patented.

Propagation:

*Type.*—By cuttings.

*Time to initiate roots.*—About seven to ten days at 26° C. to 30° C.

*Time to produce a rooted young plant.*—About four to five weeks at 22° C. to 26° C.

*Root description.*—Fibrous, medium in thickness; between 199B and N199B in color.

*Rooting habit.*—Freely branching; moderately dense.

Plant description:

*Plant form.*—Upright plant habit; long, strong and upright flowering stems.

*Growth habit.*—Vigorous; freely basal branching habit; dense and bushy growth habit; about 14 flowering stems develop per year.

*Plant height.*—About 140 cm.

*Plant width (spread).*—About 55 cm.

*Lateral branches (peduncles).*—Length: About 100 cm. Diameter: About 8 mm. Internode length: About 5.2 cm. Texture: Smooth, glabrous. Color: Close to 200B. Thorns: Density: High. Shape: Triangular with sharp acuminate apices. Height: About 8 mm. Diameter, at base: About 1.2 cm. Color, immature: Close to 187B. Color, mature: Close to 187C.

Foliage description:

*Arrangement.*—Alternate; compound with typically seven leaflets per leaf.

*Leaf length.*—About 15.5 cm.

*Leaf width.*—About 11 cm.

*Terminal leaflet length.*—About 6 cm.

*Terminal leaflet width.*—About 4 cm.

*Lateral leaflet length.*—About 5 cm.

*Lateral leaflet width.*—About 3 cm.

*Leaflet shape.*—Ovate to oval.

*Leaflet apex.*—Acute.

*Leaflet base.*—Attenuate.

*Leaflet margin.*—Serrate.

*Leaflet texture, upper and lower surfaces.*—Smooth, glabrous.

*Leaflet venation pattern.*—Pinnate.

*Leaflet color.*—Developing leaflets, upper surface: Close to 200A. Developing leaflets, lower surface: Close to 187B. Fully expanded leaflets, upper surface: Close to 139A; venation, close to 145B. Fully expanded leaflets, lower surface: Close to 147B to 147C; venation, close to 147C.

*Petioles, leaves.*—Length: About 1.1 cm. Diameter: About 2 mm. Texture, upper surface: Pubescent. Texture, lower surface: Glabrous. Color, upper surface: Close to 145C. Color, lower surface: Close to N199C.

*Petioles, leaflets.*—Length: About 2 cm. Diameter: About 1.5 mm. Texture, upper surface: Pubescent. Texture, lower surface: Glabrous. Color, upper surface: Close to N199A. Color, lower surface: Close to 148A tinged with close to 199A.

*Stipules.*—Quantity/arrangement/appearance: Two, adnate to the petiole, leafy. Length: About 2.7 cm. Width: About 3 mm. Shape: Roughly deltoid. Apex: Acuminate. Base: Truncate. Margin: Serrate, irregular. Texture, upper and lower surfaces: Smooth, glabrous. Venation pattern: Pinnate. Color, upper surface: Close to 146A tinged with close to 200C. Color, lower surface: Close to 146C.

Flower description:

*Flower type and habit.*—Red-colored flowers; consistently symmetrical rosette flowers; typically grown as a single stem.

*Flowering season.*—Year-round under greenhouse conditions, optimal flowering from spring through autumn under garden conditions; flowering intermittent.

*Flower diameter.*—About 12 cm.

*Flower depth (height).*—About 5.5 cm.

*Flower longevity on plant.*—About 30 days.

*Flower longevity as a cut flower.*—About eight to ten days; flowers persistent.

*Fragrance.*—None detected.

*Flower buds.*—Shape: Ovoid. Length: About 5.5 cm. Diameter: About 4 cm. Color: Close to 174A; towards the base, close to 144A.

*Petals.*—Quantity: Numerous; about 48 to 50 per flower. Length: About 6.2 cm. Width: About 7.1 cm. Shape: Nearly round; transversely ovate. Apex: Blunt to acute. Base: Obtuse. Margin: Entire. Texture, upper and lower surfaces: Smooth, glabrous. Color: When opening, upper surface: Close to 53A; basal spot, close to 14B. When opening, lower surface: Close to 53B. Fully opened, upper surface: Close to 46A. Older petals with a central blotch, close to 54D, 53D and 138C. Fully opened, lower surface: Close to 53B.

*Sepals.*—Quantity per flower: Typically five. Length: About 4.6 cm. Width: About 1.4 cm. Shape: Roughly deltoid. Apex: Tapered. Base: Truncate. Margin: Entire; ciliate. Texture, upper and lower surfaces: Pubescent; leathery. Color: When opening, upper surface: Between 146B and 145A. When opening, lower surface: Close to 144A tinged with close to 166B. Fully opened, upper surface: Close to 145D; towards the apex, close to 200D; central blotch, close to 45D. Fully opened, lower surface: Close to 144A; central blotch, close to 176D.

*Reproductive organs.*—Stamens: Quantity: About 200 per flower. Anther length: About 4 mm. Anther shape: Reniform. Anther color: Close to 162A. Filament color: Close to N25A; towards the apex, close to 2C. Pollen amount: Scarce. Pollen color: Close to 17C. Pistils: Quantity: About 240 per flower. Pistil length: About 1.8 cm. Stigma shape: Broadly reniform. Stigma color: Close to 160B. Style length: About 1.3 cm. Style color: Close to 154D. Receptacle height: About 1.7 cm. Receptacle diameter: About 1.6 cm. Receptacle shape: Cup-shaped. Receptacle texture: Smooth, glabrous. Receptacle color: Close to 144A. Fruits: Quantity per flower: One. Length: About 2.7 cm. Diameter: About 2 cm. Texture: Smooth. Color: Close to 146C tinged with close to 167B. Seeds: Quantity per fruit: About ten. Length: About 7 mm. Diameter: About 5 mm. Texture: Smooth. Color: Close to 153D.

Pathogen/pest resistance: Plants of the new Rose have been observed to be resistant to Powdery Mildew. Plants of the new Rose have not been observed to be resistant to pests and other pathogens common to Roses.

Temperature tolerance:

Plants of the new Rose have been observed to tolerate temperatures ranging from 0° C. to 35° C.

It is claimed:

1. A new and distinct Rose plant named 'Esm Guinda' as illustrated and described.

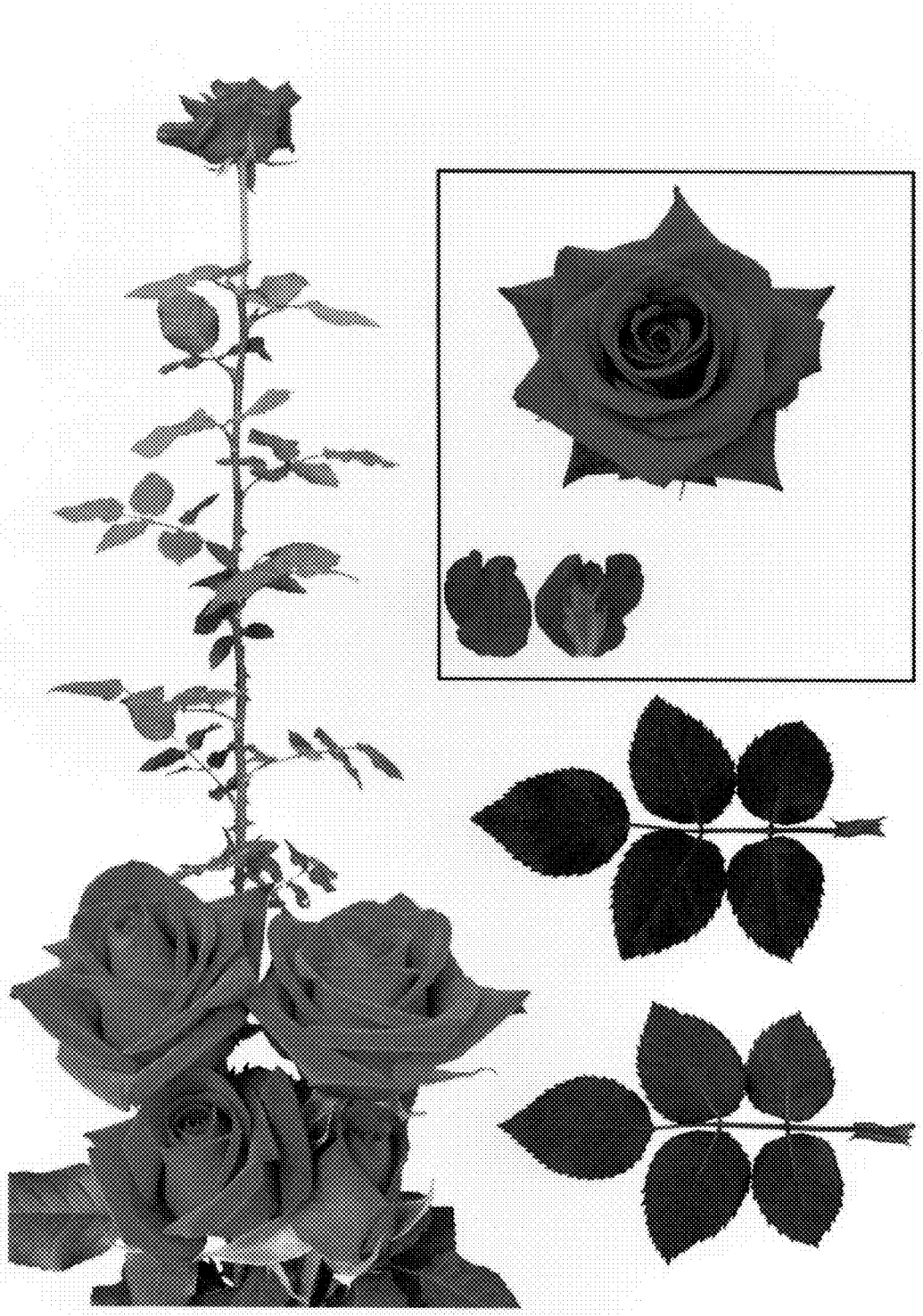

* * * * *